(12) United States Patent
Chen

(10) Patent No.: US 8,664,419 B2
(45) Date of Patent: Mar. 4, 2014

(54) ACETYLENE STORAGE USING METAL-ORGANIC FRAMEWORKS OF THE FORMULA M2(2,5-DIHYDROXYTEREPHTHALATE)

(75) Inventor: Banglin Chen, San Antonio, TX (US)

(73) Assignee: The Board of Regents of The University of Texas System, Austin, TX (US)

(*) Notice: Subject to any disclaimer, the term of this patent is extended or adjusted under 35 U.S.C. 154(b) by 280 days.

(21) Appl. No.: 13/068,075

(22) Filed: May 2, 2011

(65) Prior Publication Data

US 2011/0269984 A1    Nov. 3, 2011

Related U.S. Application Data

(60) Provisional application No. 61/343,597, filed on Apr. 30, 2010.

(51) Int. Cl.
- C07F 13/00 (2006.01)
- C07F 3/00 (2006.01)
- C07F 15/00 (2006.01)
- B01D 53/14 (2006.01)

(52) U.S. Cl.
USPC ............ 556/49; 556/131; 556/147; 95/90; 95/145

(58) Field of Classification Search
USPC ............. 556/49, 131, 147; 95/90, 145
See application file for complete search history.

(56) References Cited

U.S. PATENT DOCUMENTS

| 2007/0248852 A1 | 10/2007 | Mueller et al. ............... 95/90 |
| 2007/0252641 A1 | 11/2007 | Goodnow et al. ............ 327/543 |

FOREIGN PATENT DOCUMENTS

| JP | 2003-342260 | 12/2003 |
| JP | 2004-161675 | 6/2004 |
| JP | 2004-305985 | 11/2004 |
| WO | WO 2008/000694 | 1/2008 |

OTHER PUBLICATIONS

Bauer, et al., "Influence of connectivity and porosity on ligand-based luminescence in zinc metal—organic framework," *J. Am. Chem. Soc.*, 129:7136-44, 2007.
Bourrelly, et al., "Different adsorption behaviors of methane and carbon dioxide in the isotypic nanoporous metal terephthalates MIL-53 and MIL-47," *J. Am. Chem. Soc.*, 127:13519-21, 2005.
Britt, et al., "Highly efficient separation of carbon dioxide by a metal-organic framework replete with open metal sites," *PNAS*, 106:20637-40, 2009.
Chandler, et al., "Microporous metal-organic frameworks formed in a stepwise manner from luminescent building blocks," *J. Am. Chem. Soc.*, 128:10403-12, 2006.
Chen, et al., "A luminescent microporous metal-organic framework for the recognition and sensing of anions," *J. Am. Chem. Soc.*, 6718-9, 2008.
Chen, et al., "A triply interpenetrated microporous metal-organic framework for selective sorption of gas molecules," *Inorg. Chem.*, 46:8490-2, 2007.
Chen, et al., "High H2 adsorption in a microporous metal-organic framework with open metal sites," *Angew. Chem. Int. Ed. Engl.*, 44:4745-9, 2005.
Chen, et al., "Luminescent open metal sites within a metal-organic framework for sensing small molecules," *Adv. Mater.*, 19:1693-6, 2007.
Chen, et al., "Multiroute synthesis of porous anionic frameworks and size-tunable extraframework organic cation-controlled gas sorption properties," *J. Am. Chem. Soc.*, 131:16027-9, 2009.
Chen, et al., "Rationally designed micropores within a metal-organic framework for selective sorption of gas molecules," *Inorg. Chem.*, 46:1233-6, 2007.
Chen, et al., "Selective gas sorption within a dynamic metal-organic framework," *Inorg. Chem.*, 46:9705-9, 2007.
Chen, et al., "Surface interactions and quantum kinetic molecular sieving for H2 and D2 adsorption on a mixed metal-organic framework material," *J. Am. Chem. Soc.*, 130:6411-23, 2008.
Choi and Suh, "Highly selective $CO_2$ capture in flexible 3D coordination polymer networks," *Angew. Chem.*, 121:6997-7001, 2009.
Chui, et al., "A chemically functionalizable nanoporous material," *Science*, 283:1148-50, 1999.
Dietzel, et al., "Adsorption properties and structure of $CO_2$ adsorbed on open coordination sites of metal-organic framework $Ni_2$(dhtp) from gas adsorption, IR spectroscopy and X-ray diffraction," *Chem. Commun.*, pp. 5125-5127, 2008.
Dietzel, et al., "An in situ high-temperature single-crystal investigation of a dehydrated metal-organic framework compound and field-induced magnetization of one-dimensional metal-oxygen chains," *Angew. Chem. Int. Ed.*, 44:6354-8, 2005.
Dietzel, et al., "Hydrogen adsorption in a nickel based coordination polymer with open metal sites in the cylindrical cavities of the desolvated framework," *Chem. Commun.*, 959-61, 2006.
Dietzel, et al., "Structural changes and coordinatively unsaturated metal atoms on dehydration of honeycomb analogous microporous metal-organic frameworks," *Chemistry*, 14:2389-97, 2008.
Dincă and Long, "Hydrogen storage in microporous metal-organic frameworks with exposed metal sites," *Angew. Chem. Int. Ed. Engl.*, 47:6766-79, 2008.
Eddaoudi, et al., "Modular chemistry: secondary building units as a basis for the design of highly porous and robust metal-organic carboxylate frameworks," *Acc. Chem. Res.*, 34:319-30, 2001.
Eddaoudi, et al., "Systematic design of pore size and functionality in isoreticular MOFs and their application in methane storage," *Science*, 295:469-72, 2002.

(Continued)

Primary Examiner — Porfirio Nazario Gonzalez
(74) Attorney, Agent, or Firm — Parker Highlander PLLC

(57) ABSTRACT

This invention provides, but is not limited to, methods of using metal-organic frameworks (MOFs) having repeat units of the formula $M_2$(DHTP) (M is a divalent metal ion; DHTP=2,5-dihydroxyterephthalate) for acetylene storage. Also provided are compositions of the same formula and acetylene, e.g., an acetylene storage material comprising $[M_2(DHTP)]_n$ and acetylene.

22 Claims, 5 Drawing Sheets
(5 of 5 Drawing Sheet(s) Filed in Color)

(56) References Cited

OTHER PUBLICATIONS

Fang, et al., "A metal-organic framework with the zeolite MTN topology containing large cages of volume 2.5 nm$^3$" *Angew. Chem. Int. Ed.*, 44:3845-8, 2005.

Fang, et al., "Mesoporous metal-organic framework with rare etb topology for hydrogen storage and dye assembly," *Angew. Chem.*, 119:6758-62, 2007.

Férey, "Hybrid porous solids: past, present, future," *Chem. Soc. Rev.*, 37:191-214, 2008.

Hermes, et al., "Selective nucleation and growth of metal-organic open framework thin films on patterned COOH/CF3-terminated self-assembled monolayers on Au(111)," *J. Am. Chem. Soc.*, 127:13744-5, 2005.

Hou, et al., "Porous metal-organic framework based on mu4-oxo tetrazinc clusters: sorption and guest-dependent luminescent properties," *Inorg. Chem.*, 47:1346-51, 2008.

Huang, et al., "Shape-selective sorption and fluorescent sensing of aromatics in a flexible network of tetrakis[(4-methylthiophenyl)ethynyl]silane and AgBF$_4$," *Chem. Mater.*, 21:541-6, 2009.

Hwang, et al., "Amine grafting on coordinatively unsaturated metal centers of MOFs: consequences for catalysis and metal encapsulation," *Angew. Chem. Int. Ed.*, 47:4144-8, 2008.

Kesanli, et al., "Highly interpenetrated metal-organic frameworks for hydrogen storage," *Angew. Chem. Int. Ed. Engl.*, 44:72-5, 2004.

Kitagawa, et al., "Functional porous coordination polymers," *Angew. Chem. Int. Ed.*, 43:2334-75, 2004.

Koder, et al., "Design and engineering of an O$_2$ transport protein," *Nature*, 458:305-9, 2009.

Koh, et al., "A porous coordination copolymer with over 5000 m2/g BET surface area," *J. Am. Chem. Soc.*, 131:4184-5, 2009.

Lan, et al., "A luminescent microporous metal-organic framework for the fast and reversible detection of high explosives," *Angew. Chem. Int. Ed.*, 48:2334-8, 2009.

Lee, et al., "A comparison of the H2 sorption capacities of isostructural metal-organic frameworks with and without accessible metal sites: [{Zn2(abtc)(dmf)2}3] and [{Cu2(abtc)(dmf)2}3] versus [{Cu2(abtc)}3]," *Agnew. Chem. Int. Ed.*, 47:7741-5, 2008.

Li, et al., "Design and synthesis of an exceptionally stable and highly porous metal-organic framework," *Nature*, 402:276-9, 1999.

Lim, et al., "Cucurbit[6]uril: organic molecular porous material with permanent porosity, exceptional stability, and acetylene sorption properties," *Agnew. Chem.*, 120:3400-03, 2008.

Lin, et al., "High capacity hydrogen adsorption in Cu(II) tetracarboxylate framework materials: the role of pore size, ligand functionalization, and exposed metal sites," *J. Am. Chem. Soc.*, 131:2159-71, 2009.

Lin, et al., "Hydrogen, methane and carbon dioxide adsorption in metal-organic framework materials," *Top Curr. Chem.*, 293:35-76, 2010.

Lin, et al., "Modular synthesis of functional nanoscale coordination polymers," *Angew. Chem. Int. Ed.*, 48:650-8, 2009.

Liu, et al., "Increasing the density of adsorbed hydrogen with coordinatively unsaturated metal centers in metal-organic frameworks," *Langmuir*, 24:4772-7, 2008.

Liu, et al., "Metal-organic framework as a template for porous carbon synthesis," *J. Am. Chem. Soc.*, 130:5390-1, 2008.

Ma and Lin, "Unusual interlocking and interpenetration lead to highly porous and robust metal-organic frameworks," *Angew. Chem. Int. Ed.*, 48:3637-40, 2009.

Ma, et al., "Further investigation of the effect of framework catenation on hydrogen uptake in metal-organic frameworks," *J. Am. Chem. Soc.*, 130:15896-902, 2008.

Ma, et al., "Metal-organic framework from an anthracene derivative containing nanoscopic cages exhibiting high methane uptake," *J. Am. Chem. Soc.*, 130:1012-6, 2008.

Matsuda, et al., "Highly controlled acetylene accommodation in a metal-organic microporous material," *Nature*, 436:238-41, 2005.

Millward and Yaghi, "Metal-organic frameworks with exceptionally high capacity for storage of carbon dioxide at room temperature," *J. Am. Chem. Soc.*, 127:17998-9, 2005.

Morris and Wheatley, "Gas storage in nanoporous materials," *Angew. Chem. Int. Ed.*, 47:4966-81, 2008.

Nelson, et al., "Supercritical processing as a route to high internal surface areas and permanent microporosity in metal-organic framework materials," *J. Am. Chem. Soc.*, 131:458-60, 2009.

Noro, et al., "A new, methane adsorbent, porous coordination polymer," *Angew. Chem. Int. Ed. Engl.*, 39:2081-4, 2000.

Park, et al., "Exceptional chemical and thermal stability of zeolitic imidazolate frameworks," *Proc. Natl. Acad. Sci. USA*, 103:10186-91, 2006.

Reid and Thomas, "Adsorption kinetics and size exclusion properties of probe molecules for the selective porosity in a carbon molecular sieve used for air separation," *J. Phys. Chem. B.*, 105:10619-29, 2001.

Reid and Thomas, "Adsorption of gases on a carbon molecular sieve used for air separation: linear adsorptives as probes for kinetic selectivity," *Langmuir*, 15:3206-18, 1999.

Rosi, et al., "Hydrogen storage in microporous metal-organic frameworks," *Science*, 300:1127-9, 2003.

Rosi, et al., "Rod packings and metal-organic frameworks constructed from rod-shaped secondary building units," *J. Am. Chem. Soc.*, 127:1504-18, 2005.

Roswell and Yaghi, "Effects of functionalization, catenation, and variation of the metal oxide and organic linking units on the low-pressure hydrogen adsorption properties of metal-organic frameworks," *J. Am. Chem. Soc.*, 128:1304-15, 2006.

Samsonenko, et al., "Microporous magnesium and manganese formates for acetylene storage and separation," *Chem. Asian J.*, 2:484-8, 2007.

Seo, et al., "A homochiral metal-organic porous material for enantioselective separation and catalysis," *Nature*, 404:982-6, 2000.

Serre, et al., "Role of solvent-host interactions that lead to very large swelling of hybrid frameworks," *Science*, 315:1828-31, 2007.

Shimomura, et al., "Porous coordination polymers towards gas technology," *Struct. Bond*, 132:51-86, 2009.

Stang and Diederich, In: *Modern Acetylene Chemistry*, VCH, New York, 1995.

Tanaka, et al., "Storage and sorption properties of acetylene in jungle-gym-like open frameworks," *Chem. Asian J.*, 3:1343-9, 2008.

Thallapally, et al., "Acetylene absorption and binding in a nonporous crystal lattice," *Angew. Chem. Int. Ed. Engl.*, 45:6506-9, 2006.

Thallapally, et al., "Flexible (breathing) interpenetrated metal-organic frameworks for CO$_2$ separation applications," *J. Am. Chem. Soc.*, 130:16842-3, 2008.

Thomas, "Adsorption and desorption of hydrogen on metal—organic framework materials for storage applications: comparison with other nanoporous materials," *Dalton Trans.*, 1487-1505, 2009.

Thomas, "How far is the concept of isolated active sites valid in solid catalysts?" *Top Catal.*, 50:98-105, 2008.

Vitillo, et al., "Role of exposed metal sites in hydrogen storage in MOFs," *J. Am. Chem. Soc.*, 130:8386-96, 2008.

Wang, et al., "Enhancing H$_2$ uptake by "close-packing" alignment of open copper sites in metal-organic framework," *Angew. Chem. Int. Ed.*, 47:7263-6, 2008.

Welbes and Borovik, "Confinement of metal complexes within porous hosts: development of functional materials for gas binding and catalysis," *Acc. Chem. Res.*, 38:765-74, 2005.

Wu, et al., "High-capacity methane storage in metal-organic frameworks M2(dhtp): the important role of open metal sites," *J. Am. Chem. Soc.*, 131:4995-5000, 2009.

Xiang, et al., "Exceptionally high acetylene uptake in a microporous metal—organic framework with open metal sites," *J. Am. Chem. Soc.*, 131:12415-9, 2009.

Xu, et al., "Robust metal-organic framework enforced by triple-framework interpenetration exhibiting high H2 storage density," *Inorg. Chem.*, 47:6825-8, 2008.

Xue, et al., "New prototype isoreticular metal—organic framework Zn$_4$O(FMA)$_3$ for gas storage," *Inorg. Chem.*, 48:4649-51, 2009.

Xue, et al., "Structure, hydrogen storage, and luminescence properties of three 3D metal-organic frameworks and NbO and PtS topologies," *Crystal Growth & Design*, 8:2478-83, 2008.

(56) References Cited

OTHER PUBLICATIONS

Yildirim and Hartman, "Direct observation of hydrogen adsorption sites and nanocage formation in metal-organic frameworks," *Phys. Rev. Lett.*, 95:215504, 2005.
Zhang and Chen, "Optimized acetylene/carbon dioxide sorption in a dynamic porous crystal," *J. Am. Chem. Soc.*, 131:5516-21, 2009.
Zhang and Kitagawa, "Supramolecular isomerism, framework flexibility, unsaturated metal center, and porous property of Ag(I)/Cu(I) 3,3',5,5'-tetramety1-4,4'-bipyrazolate," *J. Am. Chem. Soc.*, 130:907-17, 2008.
Zhang, et al., "A highly connected porous coordination polymer with unusual chnnel structure and sorption properties," *Angew. Chem. Int. Ed.*, 48:5287-90, 2009.
Zhang, et al., "Versatile structure-direction roles of deep-eutectic solvents and their implication in the generation of porosity and open metal sites for gas storage," *Angew. Chem. Int. Ed.*, 48:3486-90, 2009.
Zhang, et al., "Zeolitic boron imidazolate frameworks," *Angew. Chem. Int. Ed. Engl.*, 48:2542-5, 2009.
Zhao, et al., "Hysteretic adsorption and desorption of hydrogen by nanoporous metal-organic frameworks," *Science*, 306:1012-5, 2004.
Zhou and Yildirim, "Nature and tunability of enhanced hydrogen binding in metal-organic frameworks with exposed transition metal sites," *J. Phys. Chem. C*, 112:8132, 2008.
Zhou, et al., "Enhanced H2 adsorption in isostructural metal-organic frameworks with open metal sites: strong dependence of the binding strength on metal ions," *J. Am. Chem. Soc.*, 130:15268-9, 2008.
Dybtsev, et al., "A homochiral metal-organic material with permanent porosity, enantioselective sorption properties, and catalytic activity," *Angew. Chem. Int. Ed.*, 45:916-920, 2006.
Hu, et al., "A new MOF-505 analog exhibiting high acetylene storage," *Chem. Commun.*, pp. 7551-7553, 2009.
McKinlay, et al., "Exceptional behavior over the whole adsorption-storage-delivery cycle for NO in porous metal organic frameworks," *J. Am. Chem. Soc.*, 130:10440-10444, 2008.
Banerjee, et al., "Control of pore size and functionality in isoreticular zeolitic imidazolate frameworks and their carbon dioxide selective capture properties," *J. Am. Chem. Soc.*, 131:3875-7, 2009.
Chen, et al., "Metal-organic frameworks with functional pores for recognition of small molecules," *Acc. Chem. Res.*, 43:1115-24, 2010.
International Search Report and Written Opinion, issued in PCT/US2010/023773, dated Apr. 1, 2010.
Spek, "Single-crystal structure validation with the program PLATON," *J. Appl. Cryst.*, 36:7-13, 2003.
Tanaka, et al., "Anthracene array-type porous coordination polymer with host-guest charge transfer interactions in excited states," *Chem. Commun.*, pp. 3142-3144, 2007.
Xiang, et al., "Open metal sites within isostructural metal-organic frameworks for differential recognition of acetylene and extraordinarily high acetylene storage capacity at room temperature," *Angew. Chem. Int. Ed. Engl.*, 49:4615-8, 2010.
Babarao, et al., "Storage and separation of CO2 and CH4 in silicalite, CI68 schwarzite, and IRMOF-1: a comparative study from Monte Carlo simulation," *Langmuir*, 23:659-66, 2007.
Bai, et al., "The designed assembly of augmented diamond networks from predetermined pentanuclear tetrahedral units," *Angew. Chem. Int. Ed. Engl.*, 47:5344-7, 2008.
Busker, et al., "Isomer-selective vibrational spectroscopy of benzene-acetylene aggregates: comparison with the structure of the benzene-acetylene cocrystal," *Angew. Chem. Int. Ed. Engl.*, 47:10094-7, 2008.
Caskey, et al., "Dramatic timing of carbon dioxide uptake via metal substitution in a coordination polymer with cylindrical pores," *J. Am. Chem. Soc.*, 130:10870-1, 2008.
Chen, et al., "A mircoporous metal-organic framework for gas-chromatographic separation of alkanes," *Angew. Chem. Int. Ed. Engl.*, 45:1390-3, 2006.
Couck, et al., "An amine-functionalized MIL-53 metal-organic framework with large separation power for CO2 and CH4," *J. Am. Chem. Soc.*, 131:6326-7, 2009.

Czepirski and Jagiello, "Virial-Type Thermal Equation of Gas-Solid Adsorption," *Chem. Eng. Sci.*, 44:797-801, 1989.
Eddaoudi, et al., "Porous metal-organic polyhedra: 25 A cuboctahedron constructed from 12 Cu2(CO2)4 paddle-wheel building blocks," *J. Am. Chem. Soc.*, 123:4368-9, 2001.
Fang, et al., "A multifunctional metal-organic open framework with a bcu topology constructed from undecanuclear clusters," *Angew. Chem.*, 118:6272-6, 2006.
Fang, et al., "Microporous metal-organic framework constructed from heptanuclear zinc carboxylate secondary building units" *Chem. Eur. J.*, 12:3754-8, 2006.
Férey, et al., "Hydrogen adsorption in the nanoporous metal-benzenedicarboxylate M(OH)(O2C-C6H4-CO2) (M = AI3+, Cr3+), MIL-53," *Chem. Commun.*, pp. 2976-2977, 2003.
Furukawa, et al., "Independent verification of the saturation hydrogen uptake in MOF-177 and establishment of a benchmark for hydrogen adsorption in metal-organic frameworks," *J. Mater. Chem.*, 17:3197-204, 2007.
Jagiello, et al., "Adsorption near ambient temperatures of methane, carbon tetrafluoride, and sulfur hexafluoride on commercial activated carbons," *J. Chem. Eng. Data.*, 40:1288, 1995.
Lee, et al., "Synthesis and gas sorption properties of a metal-azolium framework material," *Inorg. Chem.*, 48:9971-3, 2009.
Ma, et al., "Framework-Catenation Isomerism in MOFs and Its Impact on Hydrogen Uptake," *J. Am. Chem. Soc.*, 129:1858-9, 2007.
Mu, et al., "A novel metal-organic coordination polymer for selective adsorption of $CO_2$ over $CH_4$," *Chem. Commun.*, pp. 2493-2495, 2009.
Mulfort and Hupp, "Chemical reduction of metal-organic framework materials as a method to enhance gas uptake and binding," *J. Am. Chem. Soc.*, 129:9604-5, 2007.
Myers and Prausnitz, "Thermodynamics of mixed-gas adsorption," *AIChE J.*, 11:121-7, 1965.
Rieter, et al., "Nanoscale coordination polymers for platimun-based anticancer drug delivery," *J. Am. Chem. Soc.*, 130:11584-5, 2008.
Wang, et al., "Bottom-up synthesis a porous coordination frameworks: apical substitution of a pentanuclear tetrahedral precursor," *Angew. Chem. Int. Ed.*, 48:5291-5, 2009.
Xiao, et al., "High-capacity hydrogen and nitric oxide adsorption and storage in a metal-organic framework," *J. Am. Chem. Soc.*, 129:1203-9, 2007.
Xie, et al., "Porous coordination polyrner with flexibility imparted by coordinatively changeable lithium ions on the pore surface," *Inorg. Chem.*, 49:1158-65, 2010.
Yang and Zhong, "Molecular simulation of carbon dioxide/methane/hydrogen mixture adsorption in metal-organic frameworks," *J. Phys. Chem. B.*, 110:17776-83, 2006.
Bae, et al., "Separation of gas mixtures using Co(II) carborane-based porous coordination polymers," *Chem. Commun.*, 46:3478-80, 2010.
Chen, et al., "Porous Cu-Cd mixed-metal-organic frameworks constructed from Cu(Pyac)2[Bis[3-(4-pyridyl)pentane-2,4-dionato]copper(II)]," *Inorg. Chem.*, 43:8209-11, 2004.
Cho, et al., "A metal-organic framework material that functions as an enantioselective catalyst for olefin epoxidation," *Chem. Commun.* pp. 2563-2565, 2006.
Deng, et al., "Multiple functional groups of varying ratios in metal-organic frameworks," *Science*, 327:846-50, 2010.
Devic, et al., "Functionalization in flexible porous solids: effects on the pore opening and the host-guest interactions," *J. Am. Chem Soc.*, 132:1127-36, 2010.
Dubbeldam, et al., "Separation and molecular-level segregation of complex alkane mixtures in metal-organic frameworks," *J. Am. Chem. Soc.*, 130:10884-5, 2008.
Dybtsev, et al., "Microporous manganese formate: a simple metal-organic porous material with high framework stability and highly selective gas sorption properties," *J. Am. Chem. Soc.*, 126:32-3, 2004.
Eddaoudi, et al., "Highly porous and stable metal-organic framework: structure design and sorption properties," *J. Am. Chem. Soc.*, 122:1391-7, 2000.
Fang, et al., "Microporous metal-organic framework constructed from heptanuclear zinc carboxylate secondary building units," *Chem. Eur. J.*, 12:3754-8, 2006.

(56) References Cited

OTHER PUBLICATIONS

Finsy, et al., "Pore-filling-dependent selectivity effects in the vapor-phase separation of xylene isomers on the metal-organic framework MIL-47," *J. Am. Chem. Soc.*, 130:7110-8, 2008.

Horike, et al., "Soft porous crystals," *Nat. Chem.*, 1:695-704, 2009.

Kitaura, et al., "Immobilization of a metallo schiff base into a microporous coordination polymer," *Angew. Chem. Int. Ed. Engl.*, 43:2684-7, 2004.

Kunznicki, et al., "A titanosilicate molecular sieve with adjustable pores for size-selective adsorption of molecules," *Nature*, 412:720-4, 2001.

Li, et al., "Zeolitic imidazolate frameworks for kinetic separation of propane and propene" *J. Am. Chem. Soc.*, 131:10368-9, 2009.

Ma, et al., "Preparation and gas adsorption studies of three mesh-adjustable molecular sieves with a common structure," *J. Am. Chem. Soc.*, 131:6445-51, 2009.

Nuzhdin, et al., "Enantioselective chromatographic resolution and one-pot synthesis of enantiomerically pure sulfoxides over a homochiral Zn-organic framework," *J. Am. Chem. Soc.*, 129:12958-9, 2007.

O'Keeffe, et al., "The Reticular Chemistry Structure Resource (RCSR) database of, and symbols for, crystal nets," *Acc. Chem. Res.*, 41:1782-9, 2008.

Vaidhyanathan, et al., "A family of nanoporous materials based on an amino acid backbone," *Angew. Chem. Int. Ed. Engl.*, 45:6495-9, 2006.

Xie, et al., "Porous phosphorescent coordination polymers for oxygen sensing," *J. Am. Chem. Soc.*, 132:922-3, 2010.

Yang, et al., "Cation-induced kinetic trapping and enhanced hydrogen adsorption in a modulated anionic metal-organic framework," *Nat. Chem.*, 1:487-93, 2009.

Zhang and Chen, "Exceptional framework flexibility and sorption behavior of a multifunctional porous cuprous triazolate framework," *J. Am. Chem. Soc.*, 130:6010-7, 2008.

ACETYLENE STORAGE USING METAL-ORGANIC FRAMEWORKS OF THE FORMULA M2(2,5-DIHYDROXYTEREPHTHALATE)

The present application claims priority to U.S. Provisional Application Ser. No. 61/343,597, filed Apr. 30, 2010, the entire contents of which is incorporated herein by reference in its entirety.

This invention was made with government support under Award CHE 0718281 from the National Science Foundation and cooperative agreement 70NANB7H6178 from the National Institute of Standards and Technology. The government has certain rights in the invention.

BACKGROUND OF THE INVENTION

I. Field of the Invention

The present disclosure relates generally to the fields of chemistry and materials science. More particularly, it concerns metal-organic frameworks having repeat units of the formula $M_2(DHTP)$ (M is a divalent metal ion; DHTP=2,5-dihydroxyterephthalate), compositions thereof and methods use thereof, including acetylene storage.

II. Description of Related Art

Acetylene is an important raw material for various industrial chemicals, consumer products and for oxy-acetylene cutting in metal fabrication shops. The realization of improvements in high-density acetylene storage media are desirable. Suitable goals include increased storage capacity, safer handling, storage and transportation (Stang and Diederich, 1995; Chien, 1984).

With the realization of open structures and permanent porosity in some prototype metal-organic frameworks (MOFs) such as MOF-5 and HKUST-1 (Li et al., 1999; Chui et al., 1999), research attention has been paid to the implementation of functional sites within MOFs for their specific recognition and thus functional properties. By immobilizing open metal sites, Lewis acidic and basic sites into the pore surfaces of MOFs, a series of unique MOFs have been developed for gas storage, separation, catalysis and sensing (Rieter et al., 2008; Chandler et al., 2006; Mulfort and Hupp; 2007; Lan et al., 2009; Yildirim and Hartman, 2005; Peterson et al., 2006; Dinca et al., 2006; Zhou and Yildirim, 2008; Shou et al., 2008; Wu et al., 2009; Liu et al., 2008; Ma et al., 2008; Caskey et al., 2008; Zhang and Chen, 2008; Lin et al., 2009; Xiao et al., 2007; Chen et al., 2008a; Chen et al., 2008b; Couck et al., 2009) Because of the very explosive nature of acetylene, the nature of the interaction between specific sites within porous materials and acetylene molecules may be important for to achieve high acetylene storage at room temperature and under a pressure of 0.2 MPa (the compression limit for the safe storage of acetylene) (Budavari, 1996).

Previous efforts on porous materials and MOFs for acetylene storage have been mainly focused on those with small pores to enhance their acetylene adsorption enthalpies which have limited their uptake capacities (Reid and Thomas, 1999; Reid and Thomas, 2001; Matsuda et al., 2005; Thallapally et al., 2006; Samsonenko et al., 2007; Tanaka et al., 2008; Zhang and Kitagawa, 2008; Samsonenko et al., 2008; PCT WO 2008/000694; Zhang and Chen, 2009). Accordingly, identifying and developing methods and compositions that overcome these and other limitations are desirable.

SUMMARY OF THE INVENTION

The present disclosure provides acetylene storage materials comprising metal organic frameworks having repeat units of the formula $M_2(DHTP)$ and acetylene. Also provided are new methods of storing acetylene using organic frameworks having repeat units of the formula $M_2(DHTP)$ and acetylene.

In one aspect, the disclosure provides a method of storing acetylene comprising:
(a) obtaining a metal-organic framework (MOF) comprising a repeat unit of the formula $M_2(DHTP)$, where M is $Co^{2+}$, $Mg^{2+}$, $Mn^{2+}$, $Ni^{2+}$, $Zn^{2+}$, or a combination of one or more of these metal ions;
DHTP is:

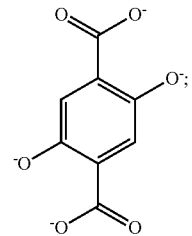

and
(b) combining the MOF with acetylene.

In another aspect, the disclosure provides acetylene storage material comprising:
(a) a metal-organic framework (MOF) comprising a repeating unit of the formula $M_2(DHTP)$, where M is $Co^{2+}$, $Mg^{2+}$, $Mn^{2+}$, $Ni^{2+}$, $Zn^{2+}$, or a combination of one or more of these metal ions;
DHTP is:

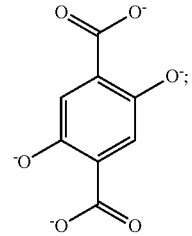

and
(b) acetylene.

In some embodiments of either of the above aspects, the MOF further comprises one or more solvent molecules. For example, the solvent can be selected from the group consisting of water, N,N'-dimethylformamide, N,N'-diethylformamide and ethanol.

In some embodiments of either of the above aspects, the MOF is at least 90% by weight is attributable to repeat units of the formula $M_2(DHTP)$. In some embodiments, the MOF is at least 95% by weight is attributable to repeat units of the formula $M_2(DHTP)$.

In some embodiments of either of the above aspects, M is $Co^{2+}$. In some embodiments, M is $Mg^{2+}$. In some embodiments, M is $Mn^{2+}$.

In some embodiments of either of the above aspects, the acetylene is substantially HC≡CH. In other embodiments, the acetylene is substantially DC≡CD.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
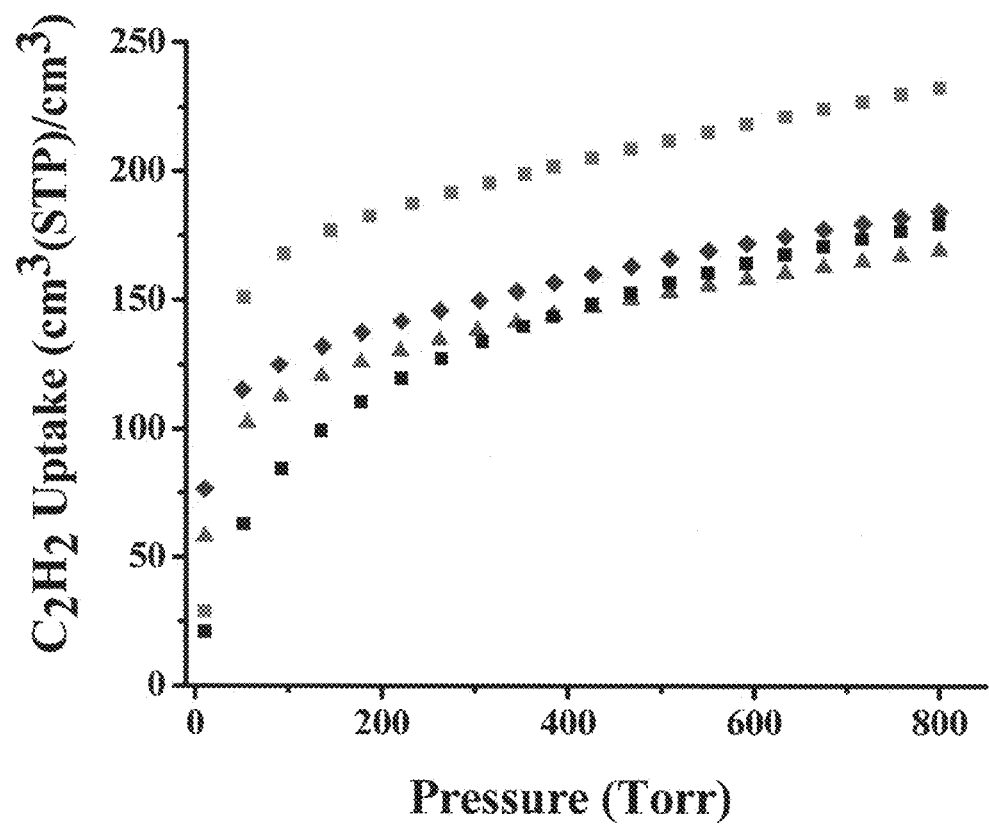
FIG. 1. Acetylene Adsorption Isotherms of Microporous MOFs. Data points correspond were taken at 295 K. The data points correspond as follows: $Co_2(DHTP)$ (red square); $Mn_2(DHTP)$ (blue diamond); $Mg_2(DHTP)$ (green triangle); HKUST-1 (black square).

Disclosed herein are methods of using metal organic frameworks having repeat units of the formula $M_2(DHTP)$ for acetylene storage and compositions thereof.

I. Definitions

"Metal-organic frameworks" (MOFs) are framework materials self-assembled by the coordination of metal ions with organic linkers exhibiting porosity, typically established by gas adsorption. The MOFs discussed and disclosed herein are at times simply identified by their repeat unit (see below), that is without brackets or the subscript n.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc.

DHTP refers to the following ligand:

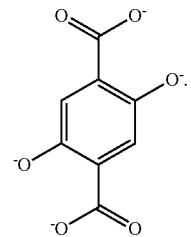

HKUST-1 corresponds to the formula $[Cu_3(TMA)_2(H_2O)_3]_n$, where TMA is benzene-1,3,5-tricarboxylate.

When used in the context of a chemical group, "hydrogen" means —H; "hydroxy" means —OH; "oxo" means =O; "halo" means independently —F, —Cl, —Br or —I; "amino" means —$NH_2$ (see below for definitions of groups containing the term amino, e.g., alkylamino); "hydroxyamino" means —NHOH; "nitro" means —$NO_2$; imino means =NH (see below for definitions of groups containing the term imino, e.g., alkylimino); "cyano" means —CN; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$—(see below for definitions of groups containing the term sulfonyl, e.g., alkylsulfonyl); "sulfinyl" means —S(O)—(see below for definitions of groups containing the term sulfinyl, e.g., alkylsulfinyl); and "silyl" means —$SiH_3$ (see below for definitions of group(s) containing the term silyl, e.g., alkylsilyl).

The symbol "—" means a single bond, "=" means a double bond, and "≡" means triple bond. The symbol "====" represents a single bond or a double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄■" means a single bond where the group attached to the thick end of the wedge is "out of the page." The symbol "......" means a single bond where the group attached to the thick end of the wedge is "into the page". The symbol "⌇" means a single bond where the conformation is unknown (e.g., either R or S), the geometry is unknown (e.g., either E or Z) or the compound is present as mixture of conformation or geometries (e.g., a 50%/50% mixture).

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≤8)}$" is two.

For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a nonaromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, CH$_2$C(O)OH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of nonaromatic nitrogen, non-aromatic oxygen, non aromatic sulfur F, Cl, Br, I, Si, and P.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and W can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

Metal-organic frameworks of the present disclosure may be made using the methods outlined below, including the Examples section. In some embodiments, [M$_2$(DHTP)(solvent)$_x$]$_n$ (M=Co$^{2+}$, Mn$^{2+}$ and Mg$^{2+}$) may be synthesized, activated accordingly to reference procedures at, for example, 200° C. under high vacuum for 12 hrs (Dietzel et al., 2005; Rosi et al., 2005; Dietzel et al., 2006; Dietzel et al., 2008; Vitillo et al., 2008, which are all incorporated herein by reference). These methods can be further modified optimized and scaled-up using the principles and techniques of chemistry and/or materials science as applied by a person skilled in the art. Such principles and techniques are taught, for example, in Eddaoudi et al. (2001), which is incorporated by reference herein.

III. Acetylene Storage Properties

Metal-organic frameworks of the present disclosure have been tested for their interactions with acetylene, including, for example, acetylene adsorption, acetylene uptake and release, acetylene storage, and binding of acetylene. Applicants note that all the MOFs disclosed and contemplated herein show a high affinity for acetylene. While the results reported below focus on binding affinity, other properties, such as costs, reliability, processability, etc., may make the use of one of these MOFs more suitable for a given application than another.

A. Acetylene Adsorption Isotherms

The acetylene uptakes of $M_2(DHTP)$ ($M=Co^{2+}$, $Mn^{2+}$ and $Mg^{2+}$) were carried out at 295 K (Chen et al., 2008a). For comparative purposes, original acetylene uptakes of $cm^3$ (STP)/g were converted to those of $cm^3(STP)/cm^3$ from their corresponding de-solvated frame densities in their single crystal X-ray data. As shown in FIG. 1, $Co_2(DHTP)$ takes up larger amount of acetylene than $Mn_2(DHTP)$ and $Mg_2(DHTP)$. The volumetric acetylene uptakes of $Co_2(DHTP)$, $Mn_2(DHTP)$ and $Mg_2(DHTP)$ at 295 K and 1 atm are 230, 182 and 167 $cm^3(STP)/cm^3$, respectively. The volumetric acetylene storage capacities of $Mn_2(DHTP)$ and $Mg_2(DHTP)$ are comparable to 177 $cm^3(STP)/cm^3$ in HKUST-1; however, that of $Co_2(DHTP)$ (230 $cm^3(STP)/cm^3$) surpasses that of HKUST-1 (177 $cm^3(STP)/cm^3$), thus increasing acetylene storage density of adsorbed acetylene in bulk material up to 0.27 $g/cm^3$, which is equivalent to the acetylene density at 25.1 MPa. Although $Co_2(DHTP)$ has slightly lower gravimetric acetylene storage capacity (22.9 wt %) than the best HKUST-1 (23.4 wt %), its higher framework density (1.169 $g/cm^3$) results in higher volumetric acetylene storage (230 $cm^3(STP)/cm^3$), exhibiting a safe acetylene storage density of adsorbed acetylene (0.27 $g/cm^3$) in bulk material at 295 K and 1 atm. This is equivalent to an acetylene density at 25.1 MPa. A comparison of these four high acetylene storage materials is shown in Table 1.

TABLE 1

Comparison of Acetylene Uptake in the Four Porous Metal-Organic Frameworks with High Acetylene Storage Capacities at 295 K and 1 atm

| MOFs (open metal site density, $mmol/cm^3$) | Acetylene Uptake ($cm^3/g$) | Framework Density $(g/cm^3)$[a] | Acetylene Uptake $cm^3(STP)/cm^3$ | wt % | Density of Adsorbed Acetylene[b] $(g/cm^3)$ | $P^{[c]}$ [MPa] |
|---|---|---|---|---|---|---|
| $Co_2$ (DHTP) (7.49) | 197 | 1.169 | 230 | 22.9 | 0.27 | 25.1 |
| $Mn_2$ (DHTP) (7.14) | 168 | 1.085 | 182 | 19.5 | 0.21 | 19.8 |
| $Mg_2$ (DHTP) (7.49) | 184 | 0.909 | 167 | 21.4 | 0.19 | 18.2 |
| HKUST-1 (4.36) | 201 | 0.879 | 177 | 23.4 | 0.21 | 19.3 |

[a]The framework density was calculated from single crystal X-ray data;
[b]Calculated density of adsorbed acetylene in bulk material.
[c]Pressure of acetylene at 295 K corresponding to the calculated density of adsorbed acetylene in bulk material.

B. Coverage-Dependent Adsorption Enthalpies

Figure 2:
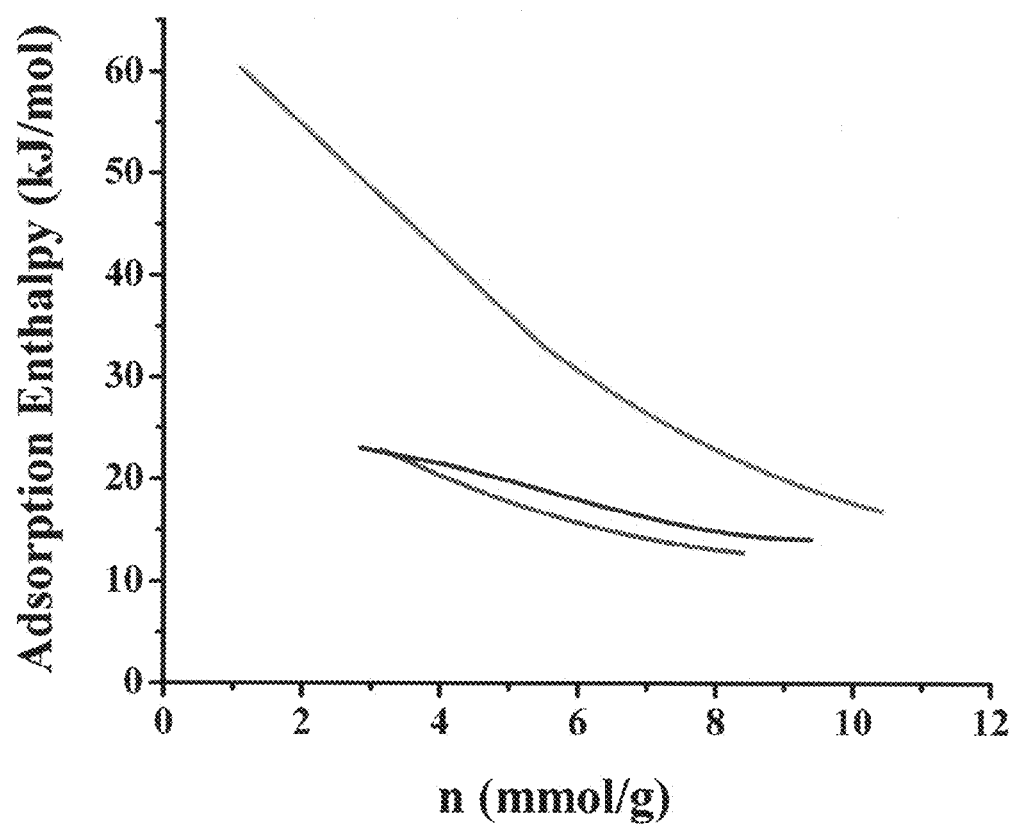
FIG. 2. Coverage Dependencies of Adsorption Enthalpies for $C_2H_2$ in MOFs. These coverage dependencies were calculated from fits of their 273 and 295 K isotherms. ($Co_2$(DHTP) (red); $Mn_2$(DHTP) (blue); $Mg_2$(DHTP) (green)).

Temperature-dependent acetylene adsorption were examined to calculate the adsorption enthalpies of these MOFs. The coverage-dependent adsorption enthalpies of the MOFs to acetylene were calculated from fits of their adsorption isotherms at 273 and 295 K (Roswell et al., 2006). The calculations are based on using virial method, a well established and reliable methodology (see Examples section below). As shown in FIG. 2, $Co_2(DHTP)$ exhibits higher adsorption enthalpies of $C_2H_2$ (60.4 kJ/mol at the coverage of 1 mmol/g) than $Mn_2(DHTP)$ (22.9 kJ/mol at the coverage of 3 mmol/g) and $Mg_2(DHTP)$ (23.0 kJ/mol at the coverage of 3 mmol/g). Without being bound by theory, such high adsorption enthalpies in $Co_2(DHTP)$ may correspond to full loading of one acetylene per open $Co^{2+}$ site even at room temperature and 1 atm, while the lower adsorption enthalpies in $Mn_2(DHTP)$ and $Mg_2(DHTP)$ indicate that higher pressure may be required to fully make use of the open $Mn^{2+}$ and $Mg^{2+}$ metal sites to maximize the acetylene storage capacities, thus the contribution of open $Co^{2+}$ sites to the acetylene storage is larger than those of open $Mn^{2+}/Mg^{2+}$ sites which is responsible for their differential acetylene uptake at room temperature and 1 atm.

The systematically high volumetric acetylene storage capacities of the three $M_2(DHTP)$ MOFs are consistent with a correlation between high open metal site density and high volumetric acetylene storage capacity.

C. Binding Sites within $Co_2(DHTP)$ for Acetylene Storage

The amount of acetylene gas adsorbed at room temperature reaches 230 $cm^3(STP)/cm^3$ at 295 K and 1 atm in $Co_2$ (DHTP), which corresponds to 1.40 $C_2H_2$ per $Co^{2+}$. $Co_2$ (DHTP) loaded with 0.54 $C_2D_2$ per Co was measured with the high resolution neutron powder diffractometer at National Institute of Standards and Technology Center for Neutron Research (NCNR). The data was analyzed using EXGUI with Rietveld refinement. Soft constraints were imposed to limit the C—C bond distance and C—H bond distance to be about 1.2 Å and 1.06 Å respectively. The bond angle constraints were also imposed to ensure that the refined $C_2D_2$ molecules are close to linear molecules.

Figure 3:
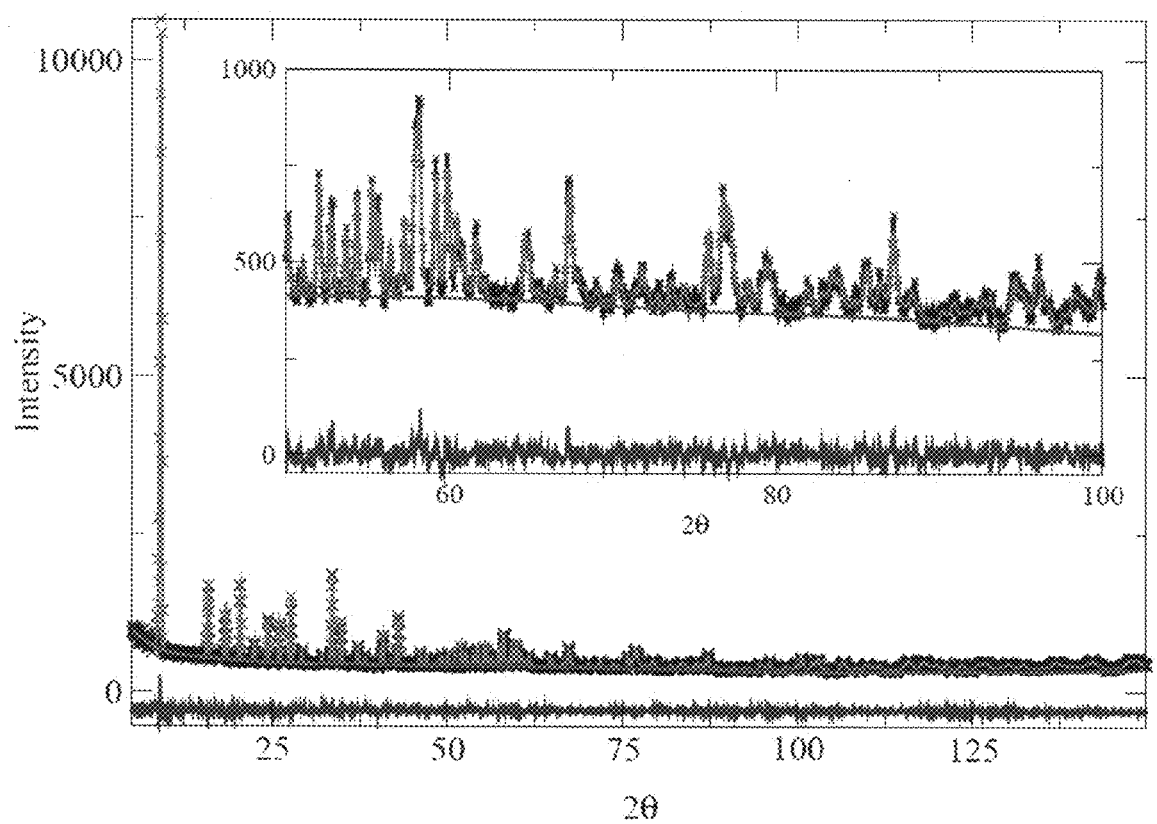
FIG. 3. Rietveld Refinement of Neutron Powder Diffraction Data for 0.54 $C_2D_2$ per Co loaded $Co_2$(DHTP). Crosses, red line, green line, and blue line represent the experimental, calculated, background, difference data points, respectively.

Based on the Rietveld refinement results ($\chi^2=0.9280$), acetylene is only adsorbed at one site at 0.54 $C_2D_2$ per Co loading, i.e., all acetylene gas molecules are adsorbed at open $Co^{2+}$ site. The experimental pattern and the calculated curves using the Rietveld method are shown in FIG. 3. The refinement results indicate that 0.54 $C_2D_2$ per Co is loaded inside the sample in good agreement of the amount of gas loaded into the material. The distance between a $C_2D_2$ molecule and the closest Co atom is about 2.62 Å, comparable to that observed between a $C_2D_2$ molecule and the closest Cu atom in HKUST-1.

Figure 4:
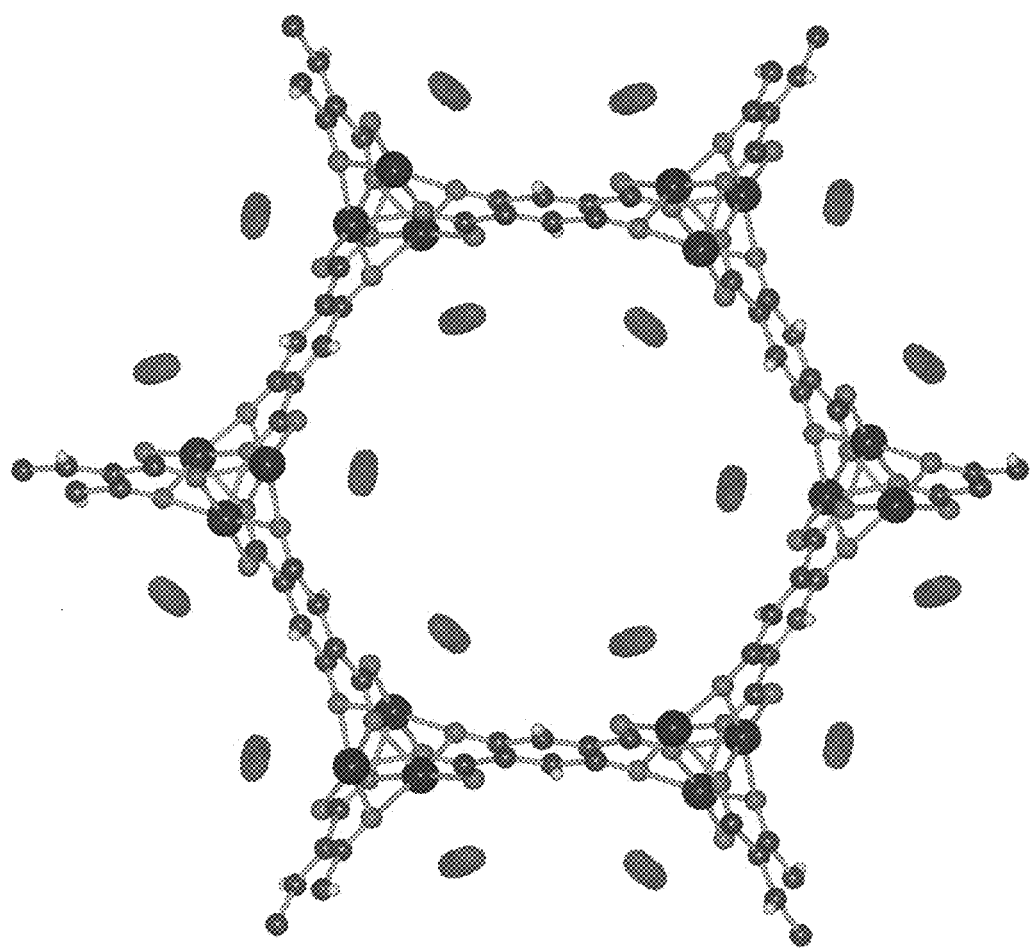
FIG. 4. Positive Difference Fourier Map of 0.54 $C_2D_2$ per Co Loaded $Co_2$(DHTP). This positive difference Fourier map was calculated from powder neutron diffraction data. The pink blobs indicate the extra positive density, which is the first adsorption site of $Co_2$(DHTP) (open Co site), after loading the acetylene gas. The blue, red, dark gray balls are Co, O, and C atoms. Atoms are not drawn to the scale.

FIG. 4 shows the Fourier difference map of acetylene adsorbed in $Co_2(DHTP)$. The pink blobs are the locations indicating additional new neutron scattering length density after introducing acetylene molecules into the sample. Without being bound by theory, the high resolution neutron powder diffraction studies on the 0.54 $C_2D_2$ per Co loaded $Co_2$ (DHTP) sample confirm that open $Co^{2+}$ sites are the first preferential acetylene storage sites.

Figure 5:
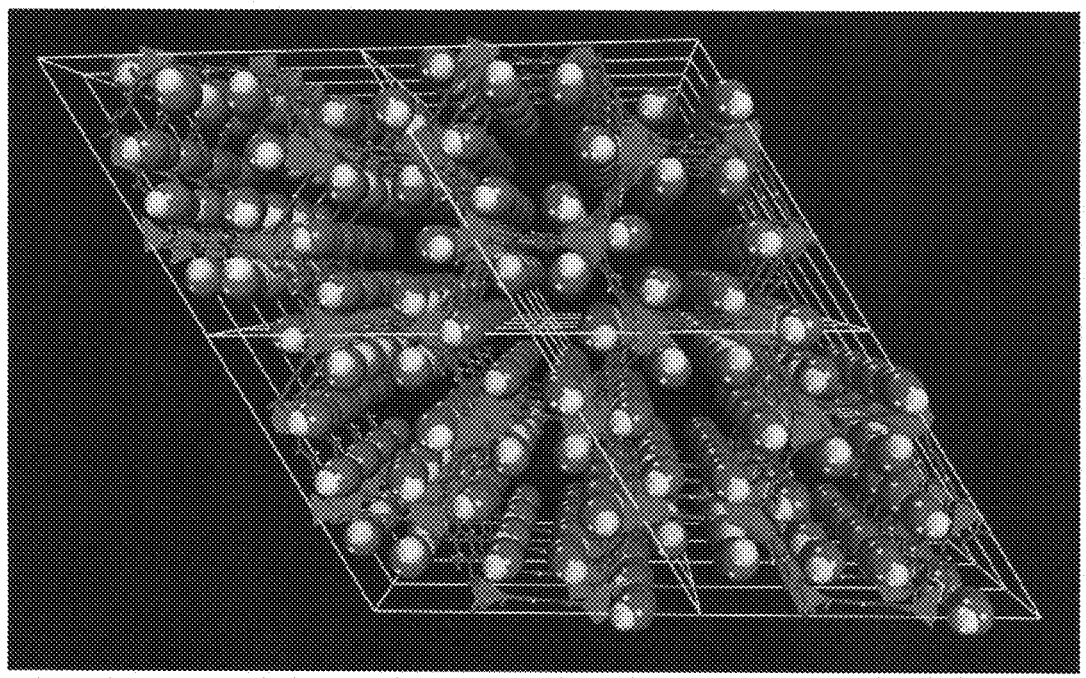
FIG. 5. Crystal structure of 0.54 $C_2D_2$ per Co loaded $Co_2$(DHTP). This figure shows the crystal structure 0.54 $C_2D_2$ per Co loaded $Co_2$(DHTP) along its c axis. The structure shows a high density of adsorbed acetylene molecules in pseudo one-dimensional arrays.

The C—C and C—H bond distance of a $C_2D_2$ molecule is 1.24 and 1.13 Å, respectively, which are comparable to those observed in $C_2D_2$ loaded HKUST-1. Unlike the basically isolated $C_2D_2$ molecules in $C_2D_2$ loaded HKUST-1, the $C_2D_2$ molecules align along the c axis as pseudo one-dimensional arrays with intermolecular $C_2D_2$ distance of about 4 Å (FIG. 5). The high density of adsorbed acetylene molecules is shown in FIG. 5 in which each 1D pore channel of 13.6 Å in diameter can encapsulate six such pseudo 1D $C_2D_2$ arrays.

D. First-Principles Total-Energy Calculations

To understand the interaction of $C_2H_2$ with different open metal sites within the three $M_2$(DHTP) (M=$Co^{2+}$, $Mn^{2+}$ and $Mg^{2+}$), first-principles total-energy calculations were performed. The density-functional theory (DFT)-derived static binding energies are summarized in Table 2, along with the C≡C bond lengths and C≡C—H bond angles of the adsorbed $C_2H_2$ molecules. While local density approximation (LDA) overestimates the binding strength and generalized gradient approximation (GGA) underestimates it, the relative binding strengths of various metals derived from the two are consistent. Among various metals investigated, $Co^{2+}$ stands out for its highest affinity to $C_2H_2$. The calculated static $C_2H_2$ binding energies on $Co^{2+}$ are 71.4 kJ/mol and 18.5 kJ/mol (corresponding to LDA and GGA results, respectively), larger than those found for Mn and Mg analogues. The calculated C≡C—H bond angle is ~167° (in contrast to the ~177-179.8° of adsorption $C_2H_2$ on other open metals), suggesting a significant polarization of the adsorbed $C_2H_2$ by the open $Co^{2+}$. The C≡C bond lengths also suggest a high degree of bond activation by the Co ion. The major contribution to the overall binding between $C_2H_2$ and the open metal ion is the Coulomb interaction between the adsorbed $C_2H_2$ dipole moment and the open metal charge density. Without being bound by theory, the strong ability of open $Co^{2+}$ to polarize and distort $C_2H_2$ molecule most likely leads to high affinity of $C_2H_2$ on $Co^{2+}$.

Table 2 summarizes data derived from our DFT calculations, including the static binding energies of $C_2H_2$ on the open metal sites in the MOFs, the C≡C bond lengths, and C≡C—H bond angles of the adsorbed $C_2H_2$ molecules.

TABLE 2

DFT Calculation Results

| | $E_B$, LDA/GGA (kJ/mol) | C≡C—H bond angle, LDA/GGA (°) | C≡C bond length, LDA/GGA (Å) |
|---|---|---|---|
| Free $C_2H_2$ | / | 180.0/180.0 | 1.200/1.208 |
| $C_2H_2$ on open $Co^{2+}$ ($Co_2$(DHTP)) | 71.4/18.5 | 167.5/166.7 | 1.228/1.232 |
| $C_2H_2$ on open $Mn^{2+}$ ($Mn_2$(DHTP)) | 55.0/17.3 | 177.2/176.9 | 1.208/1.213 |
| $C_2H_2$ on open $Mg^{2+}$ ($Mg_2$(DHTP)) | 53.0/16.9 | 179.2/178.8 | 1.204/1.210 |

IV. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Methods and Materials

Synthesis of MOFs:

$[M_2(DHTP)(solvent)_x]_n$ (M=$Co^{2+}$, $Mn^{2+}$ and $Mg^{2+}$) was synthesized, activated according to the methods below. Identity of the products was confirmed by powder X-ray diffraction study and $N_2$ adsorption isotherms. $N_2$ and acetylene adsorption isotherms were measured on a Micromeritics' ASAP 2020 Accelerated Surface Area and Porosimetry analyzer. As the center-controlled air condition was set up at 22.0 C, a water bath of 22.0° C. was used for acetylene adsorption isotherms at 295.0 K.

Synthesis of $[Co_2(DHTP)(Solvent)_x]_n$:

To a solid mixture of $H_4$DHTP (2,5-dihydroxyterephthalic acid, 0.482 g, 2.43 mmol, 1 equiv, Aldrich) and Co($NO_3$)$_2$.6$H_2O$ (2.377 g, 8.67 mmol, 3.36 equiv, Acros) was added a 1:1:1 (v/v/v) mixture of DMF-ethanol-water (200 mL) in a 500 mL screw cap jar. The suspension was mixed and ultrasonicated until homogeneous. The reaction vial was capped tightly and placed in an oven at 100° C. After 24 hours, the sample was removed from the oven and allowed to cool to RT. The mother liquor was decanted from the red-orange trigonal crystals and replaced with methanol (200 mL). The methanol was decanted and replenished four times over two days. The solvent was removed under vacuum at 250° C. over 5 hours, yielding the dark red-purple crystalline, porous material. The activated material was stored under vacuum or under an inert atmosphere.

Synthesis of $[Mg_2(DHTP)(Solvent)_x]_n$:

To a solid mixture of $H_4$DHTP (0.111 g, 0.559 mmol, 1 equiv, Aldrich) and Mg($NO_3$)$_2$.6$H_2O$ (0.475 g, 1.85 mmol, 3.31 equiv, Fisher) was added a 15:1:1 (v/v/v) mixture of DMF-ethanol-water (50 mL). The suspension was mixed and ultrasonicated until homogeneous. The reaction solution was then dispensed to five 20-mL scintillation vials. The reaction vials were capped tightly with Teflon-lined caps and placed in an oven at 125° C. After 20 hours, the samples were removed from the oven and allowed to cool to RT. The mother liquor was decanted from the yellow microcrystalline material and replaced with methanol (10 mL per vial). The yellow microcrystalline material was combined into one vial. The methanol was decanted and replenished four times over two days. The solvent was removed under vacuum at 250° C. over 5 hours, yielding the dark yellow microcrystalline, porous material. The activated material was stored under vacuum or under an inert atmosphere.

Synthesis of $[Mn_2(DHTP)(Solvent)_x]_n$:

$MnCl_2$. 4$H_2O$ (219.6 mg, 1.11 mmol, 3.3 equiv, Aldrich$_2$) and 2,5-dihydroxyterephthalic acid (66.6 mg, 0.336 mmol, 1 equiv, Aldrich) were solved in a 15:1:1 (v/v/v) mixture of DMF-ethanol-water (30 ml) in a 60 mL screw cap jar. The reaction jar was capping tightly and heated in an oven at 135° C. for 24 h. The samples were then removed from the oven and allowed to cool to RT. The reaction yielded dark orange crystalline substance. The yield is ~90% based on 2,5-dihydroxyterephthalic acid.

Neutron Powder Diffraction Studies:

As synthesized [$Co_2$(DHTP) ($H_2O$)$_2$].8$H_2O$ had been exchanged with excessive methanol for 3 days, during which the methanol solvent was changed about every 8 hours. The solvent exchanged sample was then degassed first at 200° C. degree for 48 hours and then at 250° C. degree for another 12 hours under high dynamic vacuum. After degassing, the sample was immediately transferred into a helium glove box installed with oxygen and humidity sensor, where the sample was loaded into a vanadium sample can sealed with an indium o-ring. The sample can with a valve was then mounted onto a sample stick with a gas loading line connected to an external valve. The gas loading line was evacuated to high vacuum before the sample can was pumped. During all the sample handling after the sample was degassed, the sample was not exposed to air. The sample stick was then put into a top-loading helium closed-cycle refrigerator (CCR). In order to avoid the incoherent scattering from protons, the fully deuterated acetylene ($C_2D_2$) is used in all neutron diffraction experiments. The known amount of $C_2D_2$ was first loaded to a calibrated volume and then was exposed to the sample. A temperature reading from a sensor above the sample can was recorded as the sample temperature. All the gas loading was performed at room temperature before the sample can was cooling down to 4 K for the measurements.

Total about 0.8559 g of the above activated $Co_2(DHTP)$ was used for the neutron powder diffraction experiments. The sample was measured at one gas loadings corresponding to 0.5 $C_2D_2$ per Co at room temperature. After exposing the sample to $C_2D_2$ gas, the sample was kept at room temperature for about 30 minutes to allow the acetylene gas reach equilibrium. The sample stick was then directly put into the CCR which was kept at 4 K. It took at least 10 minutes before the sample temperature reached 200 K, above which the pressure gauge already read zero. Since the boiling point of bulk acetylene is about 190 K, the inventors do not expect to have solid acetylene formed in our sample can.

Derivation of the Isosteric Heats of Adsorption:

A virial type expression of the following form was used to fit the combined isotherm data for a given material at 295.0 and 273.2 K (Roswell et al., 2006).

$$\ln P = \ln N + 1/T \sum_{i=0}^{m} a_i N^i + \sum_{i=0}^{n} b_i N^i. \quad (1)$$

Here, P is the pressure expressed in Torr, N is the amount adsorbed in mmol/g, T is the temperature in K, $a_i$ and $b_i$ are virial coefficients, and m, n represents the number of coefficients required to adequately describe the isotherms. The equation was fit using the statistical software package SPSS 16.0. m and n were gradually increased until the contribution of extra added a and b coefficients was deemed to be statistically insignificant towards the overall fit, as determined using the average value of the squared deviations from the experimental values was minimized. In all cases, m≤6 and n≤3. The values of the virial coefficients $a_0$ through $a_m$ were then used to calculate the isosteric heat of adsorption using the following expression.

$$Q_{st} = -R \sum_{i=0}^{m} a_i N^i. \quad (2)$$

Here, $Q_{st}$ is the coverage-dependent isosteric heat of adsorption and R is the universal gas constant of 8.3147 J K$^{-1}$mol$^{-1}$.

First-Principles Calculations

First-principles calculations based on density-functional theory (DFT) were performed using the PWSCF package, (Baroni et al., world-wide-web at pwscf.org.) and the detailed information was provided in the reference (Xiang et al., S.-2009).

All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

Baroni et al., http://www.pwscf.org/.
Budavari, In: *The Merck Index*, 12$^{th}$ Ed., Merck Research Laboratories, NY, 16, 1996.
Caskey et al., *J. Am. Chem. Soc.*, 130:10870, 2008.
Chandler et al., *J. Am. Chem. Soc.*, 128:10403, 2006.
Chen et al., *Angew. Chem. Int. Ed.*, 44:4745, 2005.
Chen et al., *J. Am. Chem. Soc.*, 130:6718, 2008a.
Chen et al., *J. Am. Chem. Soc.*, 130:6411, 2008b.
Chien, In: *Polyacetylene: Chemistry, Physics, and Material Science*, Academic Press, NY, 1984.
Chui et al., *Science*, 283:1148, 1999.
Couck et al., *J. Am. Chem. Soc.*, 131:6326, 2009.
Dietzel et al., *Angew. Chem., Int. Ed.*, 44:6354, 2005.
Dietzel et al., *Chem. Commun.*, 959, 2006.
Dietzel et al., *Chem. Eur. J. m* 14:2389, 2008.
Dinca et al., *J. Am. Chem. Soc.*, 128:16876, 2006.
Eddaoudi et al., *Acc. Chem. Res.*, 34:319, 2001.
Lan et al., *Angew. Chem. Int. Ed.*, 48:2334, 2009.
Li et al., *Nature*, 402:276, 1999.
Lin et al., *J. Am. Chem. Soc.*, 131:2159, 2009.
Liu et al., *Langmuir*, 24:4772, 2008.
Ma et al., *J. Am. Chem. Soc.*, 1301012, 2008.
Matsuda et al., *Nature*, 436:238, 2005.
Mulfort and Hupp, *J. Am. Chem. Soc.*, 129:9604, 2007.
PCT Appln. WO 2008/000694
Peterson et al., *J. Am. Chem. Soc.*, 128:15578, 2006.
Reid and Thomas, *J. Phys. Chem. B*, 105:10619, 2001.
Reid and Thomas, *Langmuir*, 15:3206, 1999.
Rieter et al., *J. Am. Chem. Soc.*, 130:11584, 2008.
Rosi et al., *J. Am. Chem. Soc.*, 127:1504, 2005.
Roswell and Yaghi, *J. Am. Chem. Soc.*, 128:1304, 2006.
Samsonenko et al., *Angew. Chem. Int. Ed.*, 47:3352, 2008.
Samsonenko et al., *Chem. Asian J.*, 2:484, 2007.
Stang and Diederich, In: *Modern Acetylene Chemistry*, VCH, NY, 1995.
Tanaka et al., *Chem. Asian J.*, 3:1343, 2008.
Thallapally et al., *Angew. Chem. Int. Ed.*, 45:6506, 2006.
Vitillo et al., *J. Am. Chem. Soc.*, 130:8386, 2008.
Wu et al., *J. Am. Chem. Soc.*, 131:4995, 2009.
Xiang et al., *J. Am. Chem. Soc.*, 131:12415, 2009.
Xiao et al., *J. Am. Chem. Soc.* 2007, 129:1203, 2007.
Yildirim and Hartman, *Phys. Rev. Letts.*, 95:215504, 2005.
Zhang and Chen, *J. Am. Chem. Soc.*, 130:6010, 2008.
Zhang and Kitagawa, *J. Am. Chem. Soc.*, 130:907, 2008.
Zhang et al., *J. Am. Chem. Soc.*, 131:5516, 2009.
Zhou and Yildirim, *J. Phys. Chem. C*, 112:8132, 2008.
Zhou et al., *J. Am. Chem. Soc.*, 130:15268, 2008.

What is claimed is:

1. A method of storing acetylene comprising:
   (a) obtaining a metal-organic framework (MOF) comprising a repeating unit of the formula $M_2(DHTP)$, where M is $Co^{2+}$, $Mg^{2+}$, $Mn^{2+}$, $Ni^{2+}$, $Zn^{2+}$, or a combination of one or more of these metal ions;

DHTP is:

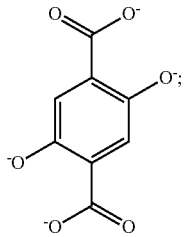

and (b) combining the MOF with acetylene.

2. The method of claim 1, where the MOF further comprises one or more solvent molecules.

3. The method of claim 2, where the solvent is selected from the group consisting of water, N,N'-dimethylformamide and ethanol.

4. The method of claim 1, where the MOF has a weight percentage at least 90% attributable to repeat units of the formula $M_2(DHTP)$.

5. The method of claim 1, where the MOF has a weight percentage at least 95% attributable to repeat units of the formula $M_2(DHTP)$.

6. The method of claim 1, where the MOF has a weight percentage at least 99% attributable to repeat units of the formula $M_2(DHTP)$.

7. The method of claim 1, where M is $Co^{2+}$.

8. The method of claim 1, where M is $Mg^{2+}$.

9. The method of claim 1, where M is $Mn^{2+}$.

10. The method of claim 1, where the acetylene is substantially HC≡CH.

11. The method of claim 1, where the acetylene is substantially DC≡CD.

12. An acetylene storage material comprising:
(a) a metal-organic framework (MOF) comprising a repeat unit of the formula $M_2(DHTP)$, where M is $Co^{2+}$, $Mg^{2+}$, $Mn^{2+}$, $Ni^{2+}$, $Zn^{2+}$, or a combination of one or more of these metal ions;

DHTP is:

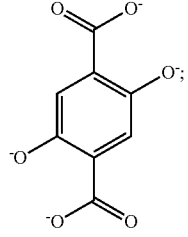

and (b) acetylene.

13. The acetylene storage material of claim 12, where the MOF further comprises one or more solvent molecules.

14. The acetylene storage material of claim 13, where the solvent is selected from the group consisting of water, N,N'-dimethylformamide and ethanol.

15. The acetylene storage material of claim 12, where the MOF has a weight percentage at least 90% attributable to repeat units of the formula $M_2(DHTP)$.

16. The acetylene storage material of claim 12, where the MOF has a weight percentage at least 95% attributable to repeat units of the formula $M_2(DHTP)$.

17. The acetylene storage material of claim 12, where the MOF has a weight percentage at least 99% attributable to repeat units of the formula $M_2(DHTP)$.

18. The acetylene storage material of claim 12, where M is $Co^{2+}$.

19. The acetylene storage material of claim 12, where M is $Mg^{2+}$.

20. The acetylene storage material of claim 12, where M is $Mn^{2+}$.

21. The acetylene storage material of claim 12, where the acetylene is substantially HC≡CH.

22. The acetylene storage material of claim 12, where the acetylene is substantially DC≡CD.

* * * * *